United States Patent [19]

Yajima

[11] 4,267,166

[45] May 12, 1981

[54] CYCLODEXTRINS AS MALODOROUS BREATH REDUCING AGENTS

[75] Inventor: Mizuo Yajima, Tokyo, Japan

[73] Assignee: Asama Chemical Co., Ltd., Tokyo, Japan

[21] Appl. No.: 127,300

[22] Filed: Mar. 5, 1980

[30] Foreign Application Priority Data

Mar. 13, 1979 [JP] Japan .................. 54-28281

[51] Int. Cl.³ .................. A61K 7/16; A61K 7/32; A61K 9/68; A61L 9/01
[52] U.S. Cl. .................. 424/48; 131/274; 131/276; 424/49; 424/76; 424/180; 424/361; 426/3; 426/486; 426/488; 426/487; 426/592; 426/638; 426/643; 426/650; 426/652; 426/660
[58] Field of Search .................. 424/48, 49–58, 424/76, 180, 361; 426/486, 487, 488, 3, 660, 592, 638, 643, 650, 652; 131/2, 17 R, 144

[56] References Cited

PUBLICATIONS

C.A. 87:28866g; 73249u (1977), 90:70803w; 70806z (1979).
C.A. 57:17092a–d (1962), 90:12181f (1979), 90:166588f (1979), 87:17296y (1977).
C.A. 64:16687a (1966), 84:147993u; 14843y; 176893s (1976).
C.A. 87:182935k (1977), 87:37667v (1977), 88:5027r, 188493g (1978), 90:92440c (1979).

*Primary Examiner*—Shep K. Rose
*Attorney, Agent, or Firm*—Blanchard, Flynn, Thiel, Boutell & Tanis

[57] ABSTRACT

A foul breath preventive agent comprising cyclodextrin as an active component.

10 Claims, No Drawings

CYCLODEXTRINS AS MALODOROUS BREATH REDUCING AGENTS

This invention relates to a foul breath preventive agent comprising cyclodextrin as an active component.

There are foods whose strong odors are apt to remain on the breath for a long time after ingestion of the foods. Examples of foods providing such foul breath include certain kinds of liquors, garlic, fish and leeks. Another example of foul breath is one caused by the nicotine smell on the breath of a heavy smoker. Foul breath sometimes arouses unpleasant feelings in people, to cause trouble, even though not serious, when an interview is being held.

Accordingly, a number of foul breath preventive agents have been heretofore developed and employed. The conventional foul breath preventive agents generally comprise perfumes as their active components. In the foul breath preventive agents of that type, the preventive effect is based on the masking effect provided by the perfume. Therefore, the malodor in the foul breath is not fundamentally eliminated, and the effect provided by the conventional foul breath preventive agents is not wholly satisfactory.

As a result of earnest studies for the purpose of searching for a foul breath preventive agent capable of providing an excellent and satisfactory preventive effect, the present inventors have found that the use of cyclodextrin as an active component for the foul breath preventive agent gives a satisfactory effect. Accordingly, the object of the invention is to provide a foul breath preventive agent having a satisfactory effect in removal of foul odors from the breath.

The cyclodextrin employed in the invention is an oligosaccharide in which a number of glucose units are connected through $\alpha$-1,4-glucoside bonding in series to form a ring structure. The cyclodextrin is generally produced by the use of a certain kind of enzyme. There are three types of cyclodextrins, and they are $\alpha$-cyclodextrin consisting of six glucose units, $\beta$-cyclodextrin consisting of seven glucose units, and $\gamma$-cyclodextrin consisting of eight glucose units. Each of these dextrins can be employed in this invention singly or in a mixture with the others.

The foul breath preventive agent comprising cyclodextrin, according to the present invention, can be used in the form of, for instance, powder, granules, pellet, capsulated agent, troche, liquid for oral use, mouth-wash, chewing gum, tooth-paste, etc. Each form can be prepared in a conventional manner.

The foul breath preventive agent according to the invention can be utilized, for example, in such a manner as swallowing, washing the inside of mouth, ingesting in the mouth, or the like. The amount of cyclodextrin taken in one time can be selected according to the strength of the odor or as required. An appropriate perfume can be employed, if desired, in combination with the cyclodextrin.

The following examples show the results of sensory tests on the foul breath preventive effect of cyclodextrin, and do not restrict the present invention.

EXAMPLE 1

The testing method was as follows:

A subject person drank about 0.36 l. of a Japanese sake (liquor), and immediately the alcoholic smell in the breath was evaluated. Subsequently, a suspension of $\beta$-cyclodextrin in the amount set forth in Table 1 in 100 ml. of water was given to the subject person to wash his mouth and gulp down. Then, the smell in the breath was evaluated in comparison with the smell evaluated prior to the ingestion of the cyclodextrin. The results are shown in Table 1.

TABLE 1

| | Amount of ingested cyclodextrin | | | |
|---|---|---|---|---|
| | 0 (water only) | 3 g | 5 g | 10 g |
| Alcoholic smell | Unchanged | Slightly reduced | Greatly reduced | Almost no smell |

EXAMPLE 2

One cooked mackerel was ingested by a subject person. The test on fishy smell in the breath was carried out in the manner described in Example 1 and the effect provided by the cyclodextrin was evaluated. The results are shown in Table 2.

TABLE 2

| | Amount of ingested cyclodextrin | | | |
|---|---|---|---|---|
| | 0 (water only) | 0.5 g | 1.5 g | 3 g |
| Fishy smell | Unchanged | Slightly reduced | Greatly reduced | Almost no smell |

EXAMPLE 3

Five pieces of fried dumpling stuffed with minced pork was ingested by a subject person. The test on garlic smell caused by the fried dumplings and remaining in the breath was carried out in the manner described in Example 1 and the effect provided by the cyclodextrin was evaluated. The results are shown in Table 3.

TABLE 3

| | Amount of ingested cyclodextrin | | | |
|---|---|---|---|---|
| | 0 (water only) | 1 g | 3 g | 5 g |
| Garlic smell | Unchanged | Slightly reduced | Greatly reduced | Almost no smell |

As is seen from the results set forth in the examples, cyclodextrin is capable of preventing a variety of smells on the breath. Accordingly, a foul breath preventive agent comprising cyclodextrin as an active component according to the invention is effective for preventing smells in the breath caused by a variety of foods or diseases.

The following examples show exemplary formulations of foul breath preventing agents of the invention, and are not understood to restrict the present invention.

EXAMPLE 4

A powdery agent was prepared by blending 1 kg. of $\beta$-cyclodextrin and 1 kg. of lactose.

EXAMPLE 5

A chewing gum comprising cyclodextrin was prepared as follows:

| | |
|---|---|
| Chewing gum base | 10 kg. |
| Powdery sugar | 22 kg. |
| $\beta$-Cyclodextrin | 10 kg. |

-continued

| | |
|---|---|
| Starch syrup | 7 kg. |
| Flavor | 0.3 kg. |

The chewing gum base was heated to 50°–60° C., and other components were added thereto. The mixture was kneaded, moulded, cooled and cut to form pieces of chewing gum.

EXAMPLE 6

A troche comprising cyclodextrin was prepared as follows:

| | |
|---|---|
| Cyclodextrin (mixture of α-, β-, and γ-forms, water content 25%) | 116 g. |
| Sugar | 116 g. |
| Tragacanth gum powder | 18 g. |
| Peppermint oil | 1 ml. |

The components set forth in the above were processed in a conventional manner to prepare troches.

EXAMPLE 7

A number of toothpastes were prepared using the formulations set forth in Table 4.

TABLE 4

| Formulation | (%) | | | | | |
|---|---|---|---|---|---|---|
| | Control | A | B | C | C | E |
| Calcium hydrogen phosphate | 40.0 | 40.0 | 40.0 | 40.0 | 40.0 | 40.0 |
| Sodium salt of carboxymethylcellulose | 1.0 | 1.0 | 1.0 | 1.0 | 1.0 | 1.0 |
| Glycerol | 25.0 | 24.0 | 22.5 | 20 | 15 | 5 |
| Cyclodextrin* | 0 | 1 | 2.5 | 5 | 10 | 20 |
| Sodium salt of saccharin | 0.2 | 0.2 | 0.2 | 0.2 | 0.2 | 0.2 |
| Sodium lauryl sulfate | 1.5 | 1.5 | 1.5 | 1.5 | 1.5 | 1.5 |
| Flavor | 0.3 | 0.3 | 0.3 | 0.3 | 0.3 | 0.3 |
| Water | 32.0 | 32.0 | 32.0 | 32.0 | 32.0 | 32.0 |

*Mixture of α-, β-, and γ-forms (content 20%; water content 25%); Celldex (trade name) CH-30, available from Nihon Shokuhin Kako Co., Ltd., Japan)

Each of the toothpastes formulated as above was evaluated by panelists consisting of people suffering from diseases of digestive organs and having the foul breath due to the diseases. The evaluation was carried out on the sensory test basis, in comparison with the control.

TABLE 5

| Formulation No. | Feeling provided after using toothpastes, regarding foul breath |
|---|---|
| A | Nearly unchanged |
| B | Slightly reduced |
| C | Reduced, and sticky feeling in the mouth diminished |
| D | Greatly reduced, and refreshed in the mouth |
| E | Almost no smell, and greatly refreshed in the mouth |

As discussed above, a foul breath preventive agent according to the invention comprises cyclodextrin as an active component. The agent may consist of cyclodextrin alone or comprise it and a conventional carrier therefor, such as sugar or the likes, chewing gum and toothpaste. It may be in various forms such as powder, tablet, liquid dispersion and liquid solution. In the case of the composition, it is preferred that a content of cyclodextrin is from 0.5 to 50% by weight.

What is claimed is:

1. A method for treating a human being having pre-existing malodorous breath which comprises orally administering to said human being, an effective, malodor-reducing amount of a composition containing, as an effective malodor-reducing ingredient, from 0.5 to 50% by weight of cyclodextrin, with the balance of said composition being edible carrier safe for oral administration to human beings, said composition being in the form of edible particles, an edible troche, an edible liquid, chewing gum or toothpaste.

2. A method as claimed in claim 1 in which said composition is swallowed by said human being.

3. A method as claimed in claim 1 in which said composition is chewing gum.

4. A method as claimed in claim 1 in which said composition is a troche.

5. A method as claimed in claim 1 in which said composition is a toothpaste.

6. A method as claimed in claim 1 in which said composition is a mouthwash.

7. A method as claimed in claim 1 in which said carrier consists essentially of water.

8. A method as claimed in claim 1 in which said human being has malodorous breath as a result of having ingested liquor or food, having smoked tobacco products or because of disease.

9. A method as claimed in claim 1, in which the cyclodextrin is in the beta-form.

10. A method as claimed in claim 1, in which the cyclodextrin is a mixture of alpha-, beta-, and gamma-forms.

* * * * *